(12) United States Patent
Michelsson

(10) Patent No.: US 7,417,719 B2
(45) Date of Patent: Aug. 26, 2008

(54) METHOD, DEVICE AND SOFTWARE FOR THE OPTICAL INSPECTION OF A SEMI-CONDUCTOR SUBSTRATE

(75) Inventor: Detlef Michelsson, Wetzlar-Naunheim (DE)

(73) Assignee: Leica Microsystems Semiconductor GmbH, Wetzlar (DE)

( * ) Notice: Subject to any disclaimer, the term of this patent is extended or adjusted under 35 U.S.C. 154(b) by 428 days.

(21) Appl. No.: 10/546,372

(22) PCT Filed: Jan. 13, 2004

(86) PCT No.: PCT/EP2004/000154

§ 371 (c)(1),
(2), (4) Date: Aug. 19, 2005

(87) PCT Pub. No.: WO2004/074822

PCT Pub. Date: Sep. 2, 2004

(65) Prior Publication Data

US 2006/0176476 A1    Aug. 10, 2006

(30) Foreign Application Priority Data

Feb. 21, 2003    (DE) .............................. 103 07 454

(51) Int. Cl.
*G01N 21/00* (2006.01)
(52) U.S. Cl. ................................ 356/237.1; 356/237.2
(58) Field of Classification Search ......... 356/402–425, 356/237.1–237.6; 382/144–154; 250/559.4, 250/559.41, 559.45, 226, 559.46
See application file for complete search history.

(56) References Cited

U.S. PATENT DOCUMENTS

| | | | |
|---|---|---|---|
| 4,992,949 A * | 2/1991 | Arden | 700/223 |
| 5,140,412 A | 8/1992 | Shishido et al. | |
| 5,802,361 A | 9/1998 | Wang et al. | |
| 5,892,241 A | 4/1999 | Moriya | |
| 5,998,801 A * | 12/1999 | Imai | 250/548 |
| 6,795,573 B2 * | 9/2004 | Yoshida | 382/149 |
| 6,882,416 B1 * | 4/2005 | Hunter et al. | 356/237.4 |
| 2002/0110276 A1 | 8/2002 | Kasutami | |

FOREIGN PATENT DOCUMENTS

EP    0 883 030 A2    12/1998

* cited by examiner

*Primary Examiner*—Gregory J Toatley, Jr.
*Assistant Examiner*—Tri T Ton
(74) *Attorney, Agent, or Firm*—Houston Eliseeva LLP

(57) ABSTRACT

The invention relates to a method and a device for the optical inspection of the surface of semi-conductor substrate. An image (1) is captured on the surface of the semi-conductor substrate which is covered with a thin layer. Said image is made of a plurality of pixels having associated colour values and intensities. The frequency distribution of pixels having equal colour co-ordination values is calculated (3,4,5) from the colour values in a colour range (2), said colour range having a colour intensity and colour co-ordinates. The thus calculated frequency distribution is used (7, 9) to compare a second correspondingly calculated frequency distribution or a variable derived therefrom. According to the invention, the colour shift (9) and/or differences (7) in the colour distribution are determined according to fluctuations in the intensity of the illumination. The invention also relates to a method and a device for producing a structured semi-conductor substrate by using the above-mentioned method or the above-mentioned device and software for carrying out said method.

27 Claims, 6 Drawing Sheets

METHOD, DEVICE AND SOFTWARE FOR THE OPTICAL INSPECTION OF A SEMI-CONDUCTOR SUBSTRATE

The invention relates to a method, a device, and a software for the optical inspection of the surface of a semiconductor substrate, as well as to a method and a device to produce a structured semiconductor substrate that uses such a method and/or such a device.

Semiconductor components are generally produced in a multiplicity of processing steps. Thin layers are repeatedly applied to the surface of a semiconductor substrate, for example, photoresist layers, thin metallized coatings, or dielectric layers. To achieve a high level of consistent quality, the thin layers must be applied at a consistent quality. In modern semiconductor technology, a plurality of semiconductor components are generally produced on a single wafer. Individual wafer substrates are illuminated with the help of a stepper, and the illumination step is repeated several times. Consistent quality of illumination requires a homogeneous surface covering, particularly in the application of a homogeneous photoresist layer on the wafer. For this reason, it is desirable to have a simple means of assessing quality of thin layers on a semiconductor substrate, in particular their homogeneity.

Because of interference effects, thin layers reflect light with color. As a result, if the surface of a semiconductor substrate with thin layers is illuminated and the reflected light analyzed, inhomogeneities in the thickness of the layer can be detected as color variances.

A method is known from the state of the art for using macroscopic images of the surface of a semiconductor substrate covered with thin layers to determine mean values and color dispersions, and to compare these with each other and with a reference wafer. Fluctuations in the brightness of the illumination, however, lead to fluctuations in the brightness of the reflected light so that the mean values for colors in the RGB range are in principle dependent on brightness. In addition, mean values and dispersion describe only a portion of the color changes that occur.

The task of the present invention is to create a method, a software program, and a device for the optical inspection of the surface of a semiconductor substrate in order to determine even more reliably processing defects in the application of thin layers to a semiconductor substrate. In addition, a method and a device to produce a structured semiconductor substrate are to be created that permit the production of semiconductor components of consistently high quality.

This task is solved by a method with the characteristics according to claim 1 and 13 or 14, respectively, by a software program according to claim 28 for implementing the method, as well as by a device with the characteristics according to claim 15 and 26 or 27, respectively. Other advantageous embodiments of the invention are the subject of the related subordinate claims.

According to the invention, to optically inspect the surface of a semiconductor substrate to which a thin layer has been applied, an image that is made up of a plurality of pixels is captured of the surface of the semiconductor substrate, each with at least three associated intensities of varying wavelength that are designated as color values; a frequency distribution of pixels with the same color coordinate values is calculated from the color values by transformation in a color range spanning one intensity and color coordinates; and the frequency distribution calculated therefrom is used for comparison with a second calculated frequency distribution or with a variable derived therefrom.

The advantage is that the result of the comparison is independent of the intensity of the light reflected from the surface of the semiconductor substrate, and therewith independent of fluctuations in the illumination, because the intensity of the pixels does not have to be considered when calculating the frequency distributions. According to the invention, processing defects in applying thin layers to a semiconductor substrate can therefore be determined even more reliably. As a result of processing defects, inhomogeneities in the thickness of the layers may, for example, occur, or layers may be missing. Processing defects may also occur as a result of defocusing during illumination of the semiconductor substrate. In particular, the intensity of the illumination used to capture images can be changed, according to the invention, in order, for example, to effect resolution of various defects on the surface of the semiconductor substrate without having it significantly affect the calculated frequency distribution. Various angles of incidence may be used for illumination, in so far as the angle is the same as when teaching a reference wafer.

It is particularly preferable that three color values, i.e., intensities of varying wavelengths with the color range spanning one intensity and two color coordinates be associated with each pixel. However, this is not a limitation on the present invention. Rather, the present invention can in principle be applied to ranges with higher dimensions, not merely to the three-dimensional range. For example, four color values can also be associated with the pixels.

To capture images, a conventional color imaging sensor of suitable spectral sensitivity such as a color camera, video camera, CCD sensor, or one-dimensional color line scanner can be used to create a digital image composed of pixels with associated color values. Very preferably, RGB components spanning a three-dimensional range are associated with each pixel.

Intensities with three other wavelengths that lie completely or partially in the ultraviolet and/or infrared wavelength range of light can be used in place of the RGB components. "Color" imaging sensors of suitable spectral sensitivity are used for that purpose.

Depending on the specific requirements, the color imaging sensor is used to capture a macroscopic image of the entire surface of the semiconductor substrate or of a suitable subarea thereof. For this purpose, the imaging range of the color imaging sensor can also be changed depending, for example, on the requirements of each comparison being conducted. The color imaging sensor can be coupled with a suitable imaging device such as a microscope.

The second frequency distribution used for the comparison can, for example, be calculated and stored on the basis of at least one image of a reference wafer of satisfactory quality. The second frequency distribution can also be calculated, for example, on the basis of at least one image of a second wafer from a current processing batch or portion thereof. In addition, the second frequency distribution can also be calculated on the basis of at least one image of a range of the current wafer that is subject to inspection. It is also possible to compare the frequency distribution of the reference wafer images with the current wafer, in which case local and global color variances can be determined simultaneously. It is advantageous that the method according to the invention can be very flexibly adapted to the specific requirements of the comparison being conducted.

Preferably, the RGB components of the pixel color values are transformed in the color range by means of linear transformation, which saves on calculation time. In addition, color deviations or color shifts derived from the comparison can be better compared with each other as a result. Preferably, the frequency distribution and/or the second frequency distribution used for the comparison is calculated by totaling the frequency of the occurrence of pixels with the same color coordinate values in the color range. Preferably, the frequency distribution corresponds to a two-dimensional histogram in the color range used.

According to a particularly preferred embodiment of the invention, the color range used is a YUV color range, whereby Y corresponds to the light intensity or luminescence of the pixels, and Y itself is not considered when calculating the frequency distribution. It is advantageous that the YUV color range is used in the state of the art to code color images and color videos. Efficient and inexpensive chips are available for video processing as well as for image compression hardware for the method according to the invention.

However, the present invention is in principle not limited to the use of a YUV color range. Rather, other color ranges known from the state of the art can be used, such as the YIQ color range, YCbCr color range, or the like. However, linear transformation of the pixel color values in the color range is particularly preferred for effecting transformation.

If the color values for the colors red (R), green (G), and blue (B) are not detected in the RGB color range, but in other spectral regions, comparable mathematical transformations can be used to transform the color values in the color range being evaluated, according to the invention.

Preferably, the frequency distribution calculated in the color range and used for the comparison is smoothed by using a filter such as a box filter. It is advantageous that the resultant noise elicited by fluctuations in the frequency distribution be suppressed or at least lessened, which increases the precision of the method still further.

As is well known, a plurality of semiconductor components or dies is applied to a wafer in the engineering of semiconductors. According to the invention, and depending on the specific requirements, it is preferable according to the invention that the frequency distribution be alternatively calculated on the basis of images captured of at least one semiconductor substrate comprising a plurality of semiconductor components or dies, or of a surface area illuminated in a stepper illumination step (stepper area window; SAW) of the semiconductor substrate; or of an individual die; or of a subarea of a die. The areas used for capturing images can preferably be combined in any manner to calculate the first and the second frequency distribution. For example, the first frequency distribution may be calculated on the basis of an image of a single die or of a SAW, while the second frequency distribution is calculated on the basis of an image of the entire surface of a reference wafer. This permits one to compare the quality of individual semiconductor components with each other on one and the same wafer; for example, of adjacent semiconductor components or of selected components on the substrate or wafer.

According to a first embodiment of the invention, a center of gravity is calculated for the comparison from the calculated frequency distributions, and the position of the center of gravity is compared with the position of the center of gravity of the second frequency distribution in order to detect a color shift from which conclusions may be drawn, for example, regarding systematic fluctuations in thickness of thin layers on the same semiconductor substrate. The second frequency distribution can be calculated on the basis of an image of a reference wafer or, for example, of an adjacent semiconductor component on the surface of the same semiconductor substrate. The centers of gravity in the color range used represent simple coordinate values that can easily be compared with one another. As a result, color shifts can be detected reliably with a high level of precision.

According to a second embodiment of the invention, the calculated frequency distribution is subtracted from the second frequency distribution to make the comparison in order to detect differences in color distribution for the semiconductor substrate. The second frequency distribution can be calculated on the basis of an image of a reference wafer or, for example, of an adjacent semiconductor component on the surface of the same semiconductor substrate. It is advantageous that differences in the frequency distributions can be more easily detected and resolved by generating difference. In order to bring out such differences, the difference can, for example, be further intensified by multiplication by a predetermined factor.

Obviously, the first and second embodiments of the invention may be combined with each other.

Furthermore, an alarm signal, a variable, or the like can be created when a detected color shift according to the first embodiment and/or the differences detected in color distribution of the semiconductor substrate according to the second embodiment exceed a predetermined threshold value. The alarm signal, the generated variable, or the like can thus be enlisted to automatically interpret the inspection process, for example, in a device that produces a structured semiconductor substrate, such as is used on semiconductor production lines that are well known from the state of the art.

According to a further embodiment of the invention, the threshold value used may be calculated by averaging the frequency distributions of surface areas that are geometrically arranged in a given configuration on a wafer. A radial distribution of the surface areas used is particularly preferable. In this way, effects that lead to radially-dependent heterogeneous layer thickness on a wafer, for example as a result of spin coating a photoresist layer, can be easily taken into account.

Obviously, any i moments of the calculated frequency distributions can be used for the comparison, whereby i is a whole number and $i \geq 1$.

To implement the method according to the invention, a device for the optical inspection of the surface of a semiconductor substrate comprises a suitable imaging sensor of suitable spectral sensitivity such as a color camera, video camera, or CCD sensor; suitable computational devices such as microprocessors, special processors, or the like; and suitable means of comparison such as microprocessors, specialty processors, or the like.

According to a further embodiment of the invention, the method according to the invention can be reduced to practice with the help of software and/or a computer program that comprises a program code in order to implement the steps of the method according to the invention when the software or the computer program is implemented in a computer or other suitable data processing mechanism to control the computational device and means of comparison. Preferably, the software and/or the computer program comprises a program code that can be stored on a storage medium that can be read by a computer.

An example of a preferred embodiment of the invention is described below on the basis of the appended figures, wherein.

The method according to the invention serves to optically inspect the surface of a semiconductor substrate 21, for example, a semiconductor wafer whose surface is covered with one or several thin layers such as a photoresist layer, a metallization, a dielectric layer, or the like. Interference effects impart to the surface a color that is dependent on the thickness of the thin layer. As a result, the light reflected from the surface permits one to draw conclusions regarding the thickness of the thin layer. Color variances in the reflected light intensity permit one to draw conclusions regarding inhomogeneities in the thickness of the thin layer.

The surface of the semiconductor substrate 21 or a portion of the surface, such as a so-called stepper area window (henceforth SAW) that comprises a plurality of dies or semiconductor components, or an area with one or several dies, or a part of a die, can be macroscopically captured with the help of a CCD camera 1 that serves as a color imaging sensor. The image information is comprised of a plurality of pixels with associated color values and intensities.

Figure 2:
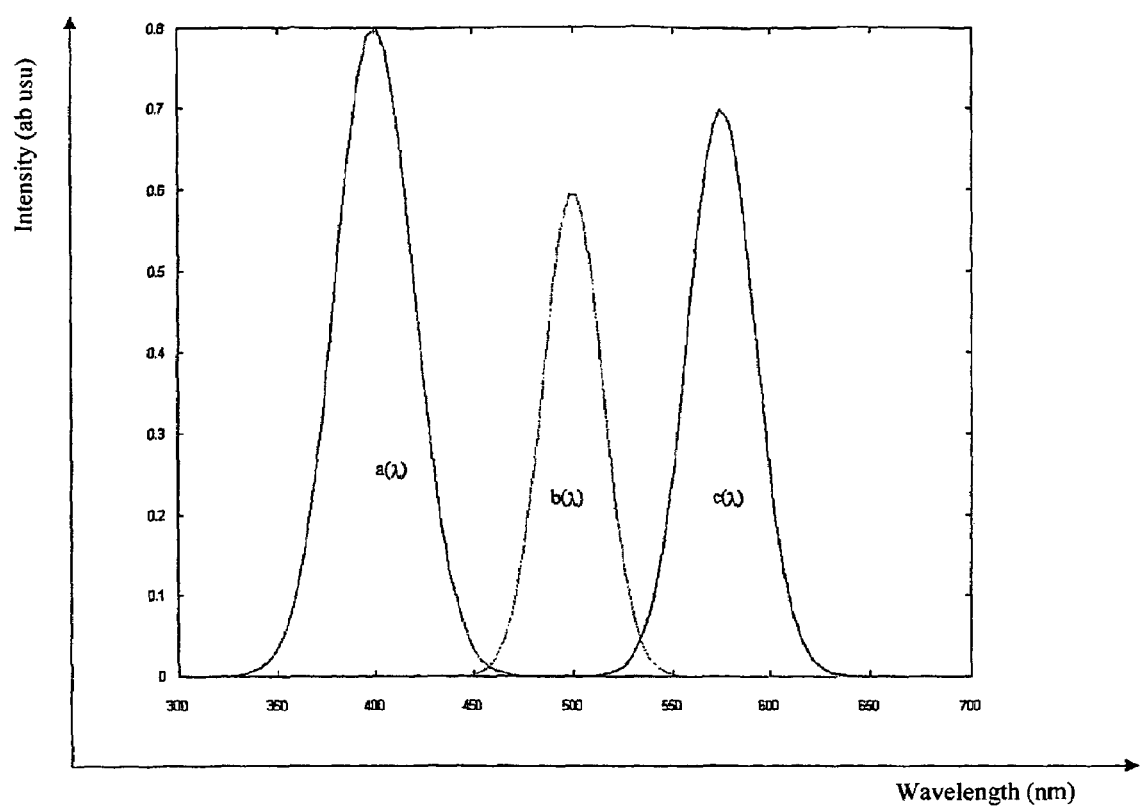
FIG. 2 depicts the spectral sensitivity of a sensor camera that detects light at three different wavelengths in the visible spectral region.

FIG. 2 represents the spectral sensitivity of a sensor camera 1 that detects light at three different wavelengths in the visible spectral region, namely for the colors red, green, and blue. The color camera 1 provides three intensity values for each pixel in the color image. The value of each channel is dependent on the spectral sensitivity of the individual sensors and on the incident light. FIG. 2 shows the spectral sensitivity of a 3-sensor camera 1, whose sensors A, B, and C are sensitive to visible light.

If $\phi_\lambda$ is the spectral distribution of the incident light, sensors A, B, and C provide the following intensities:

$$I_A = k \cdot \int_o^\infty a(\lambda)\phi_\lambda(\lambda)d\lambda$$

$$I_B = k \cdot \int_o^\infty b(\lambda)\phi_\lambda(\lambda)d\lambda$$

$$I_C = k \cdot \int_o^\infty c(\lambda)\phi_\lambda(\lambda)d\lambda$$

whereby k is an amplification factor.

The image information is entered into an image processing device that transforms the RGB components of the image information into the YUV color range.

The YUV color range is the basis for color coding in the television norms used in Europe and is known to be comprised of the RGB components of the image information as follows:

$$Y = 0.299R + 0.587G + 0.114B$$

$$U = -147R - 0.289G + 0.437B = 0.493(B-Y)$$

$$V = 0.615R - 0.515G - 0.100B = 0.877(R-Y)$$

The Y components represent luminescence. The YUV color range thus spans the intensities and the color coordinates U, V.

Figure 1:
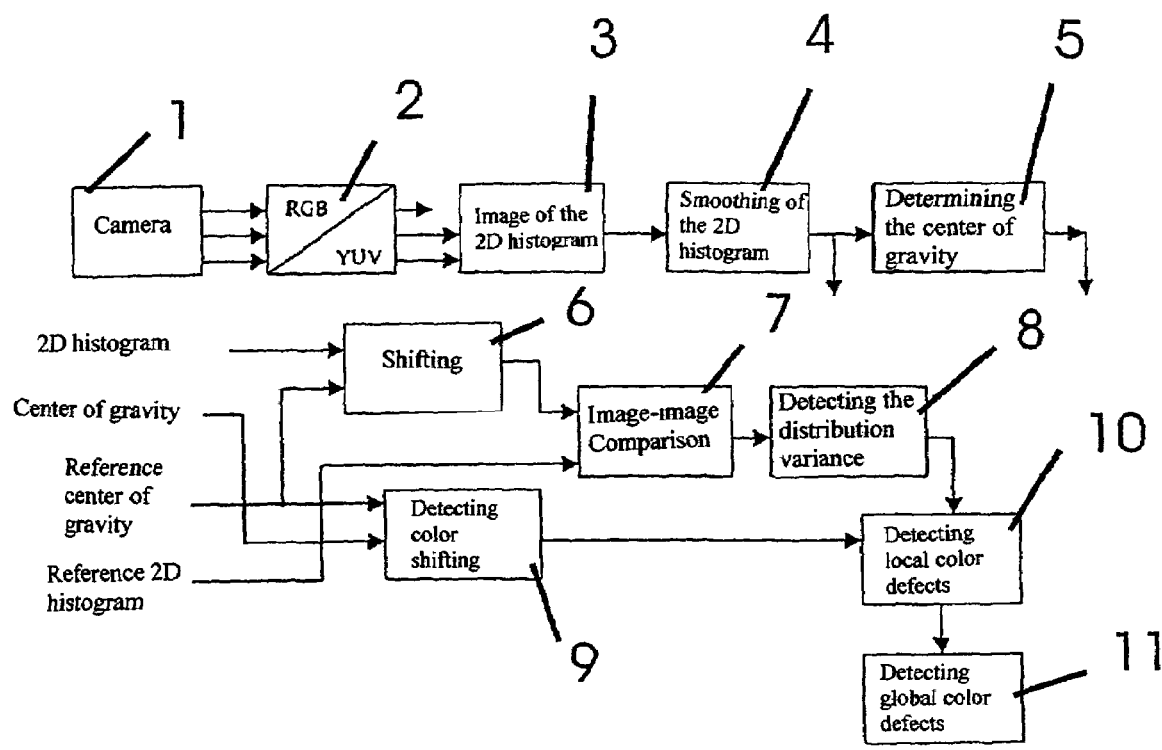
FIG. 1 depicts a schematic block diagram of a device to implement the method according to the invention.
Figure 3:
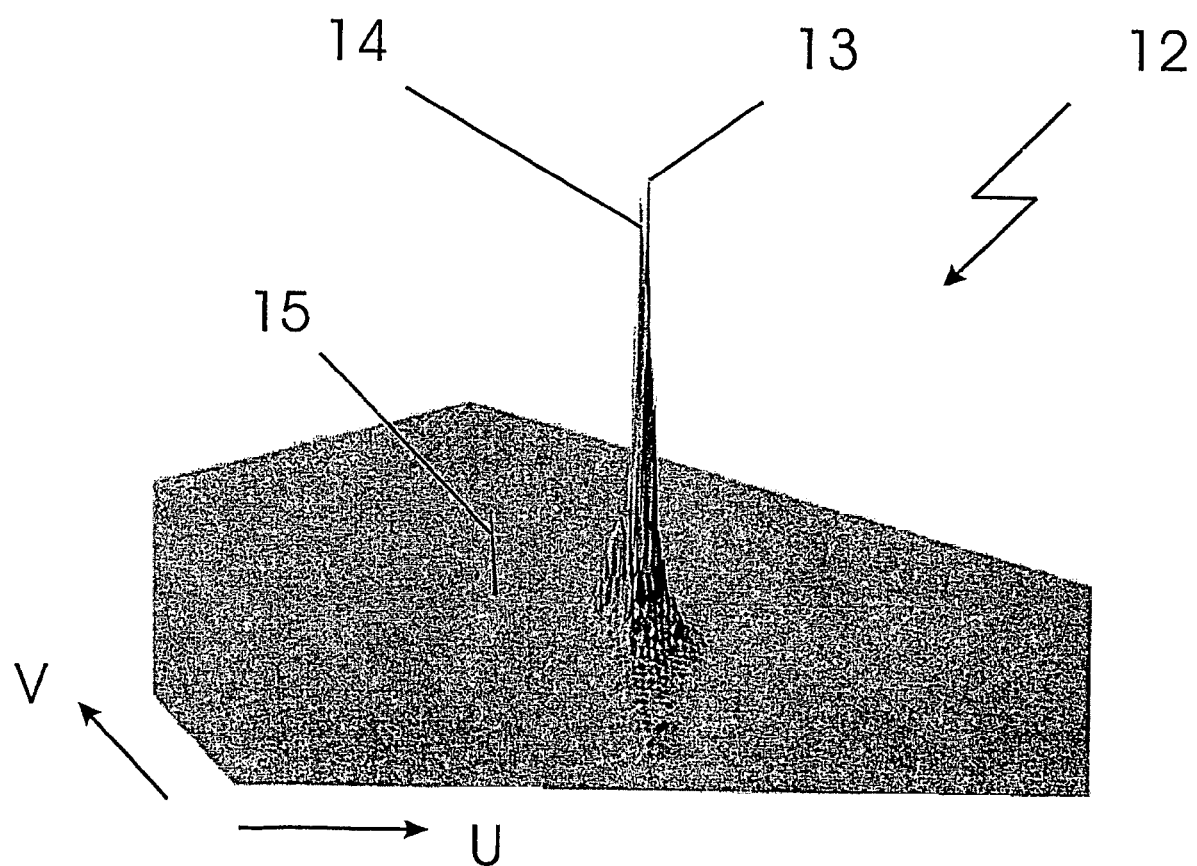
FIG. 3 depicts a two-dimensional histogram in a YUV color range that is calculated with the help of the device depicted in FIG. 1.

The Y component is not considered during further processing of the image information, which is indicated in FIG. 1 by the incomplete arrow between blocks 2 and 3. The remaining U and V color coordinate values span a two-dimensional range of color. The frequency of the occurrence of a pixel with the same U and V values for each captured image area is totaled with the help of a computational device 3. Thus the frequency distribution 12 (histogram) depicted in FIG. 3 is calculated in the two-dimensional color range. The frequency distribution 12 exhibits two peaks 13, 14 as well as one subordinate peak 15 that is attributable to image artifact.

Because digital image processing is capable of only limited resolution, the calculated frequency distribution 12 exhibits discrete steps. Depending on the resolution used, for example 8-bit, the calculated frequency distribution 12 is overlaid with a discrete noise that can interfere with subsequent comparisons and that leads to the double peaks 13, 14 in FIG. 3.

The calculated frequency distribution 12 is smoothed with the help of a filter 4, for example with the help of a box filter. Suitable alternative filter algorithms will be clear to a person skilled in the art examining this description, and requires thus no further explanation.

Figure 4:
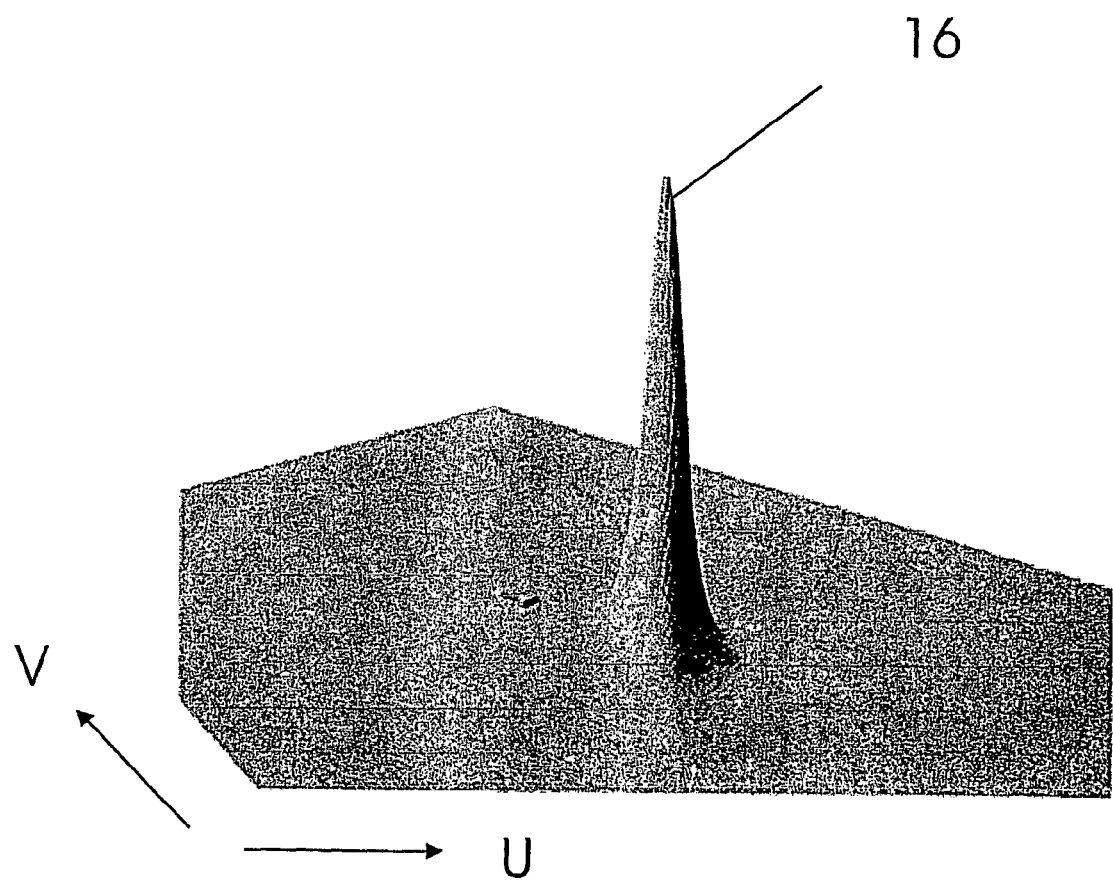
FIG. 4 depicts the two-dimensional histogram according to FIG. 3 after smoothing.

FIG. 4 shows schematically the smoothed frequency distribution 12 according to FIG. 3. Depending on the width of the set frequency window of the filter 4, a small amount of negligible spreading of the frequency distribution 12 will occur such that double peaks 13, 14 converge into a single peak 16 in FIG. 4.

The center of gravity of the calculated frequency distribution 12, expressed in U and V color coordinates, can be determined with the help of the other computational device 5. In the color range spanned by the U and V color coordinates, each position corresponds to a color of the reflected light intensity. If the light is reflected as many colors, the smoothed frequency distribution 12 exhibits more than one peak.

The subsequent processing steps of the method according to the invention are depicted schematically in the lower part of FIG. 1. For the comparison step carried out alternatively in block 7 or 9, the method uses a second frequency distribution (reference 2-dimensional histogram). The second frequency distribution is calculated on the basis of light that is reflected from a reference region, depending on the requirements of the method; alternatively on the basis of light that is reflected from a reference wafer with good surface characteristics or a surface section thereof; from an illuminated surface area (SAW) of the reference wafer or a semiconductor substrate 21 thereof in a stepper illumination step; or from a single die or a section thereof of a reference wafer or the semiconductor substrate 21 thereof. The calculation is done in the aforementioned manner, in particular by using identical or comparable illumination conditions and/or a smoothing step. The second frequency distribution can be stored in a storage medium.

The position of the center of gravity (reference center of gravity) can also be calculated for the second frequency distribution in the aforementioned manner.

If the position of the center of gravity of the frequency distribution 12 and the reference frequency distribution 12 are not identical, this results in a color shift of the light reflected by the semiconductor substrate 21 in comparison to the light reflected by the reference region. This color shifts is determined by block 9 by the difference generated between the two centers of gravity.

Depending on the reference region used and the imaging area used to calculate the frequency distribution 12, this color shift can be used in subordinate block 10 to determine local color defects or in subordinate block 11 to detect global color defects. Local color defects which may, for example, be elicited by localized bulging of the thin layer because of a dust speck, may, for example, be detected by comparing the frequency distributions of two local surface areas of one and the same wafer, or by the appearance of an additional peak in the frequency distribution 12 of the semiconductor substrate 21 being tested. Global color defects, on the other hand, lead to a systematic color shift of the peak or of all peaks in the semiconductor substrate 21 that is to be tested in comparison to a reference wafer. Systematic color shifts may occur both as a result of changed layer thicknesses or missing layers, or in cases of incorrect layers through the use of an incorrect reticle.

Alternatively or additionally, the calculated frequency distribution 12 for the semiconductor substrate 21 to be tested can also be shifted from block 6 in such a way that its center of gravity is congruent with the reference center of gravity. The shifted frequency distribution 12 in block 7 is then compared with the second frequency distribution (reference two-dimensional histogram). For this purpose, both frequency distributions can be overlaid on each other in block 7. In the case of local color shifting, an additional peak, for example, can occur in the frequency distribution 12 of the semiconductor substrate 21 to be tested after overlaying, which can lead to two peaks of unequal height in the overlaid total frequency distribution 12, which is comparable to the distribution 12 according to FIG. 5.

Figure 5:
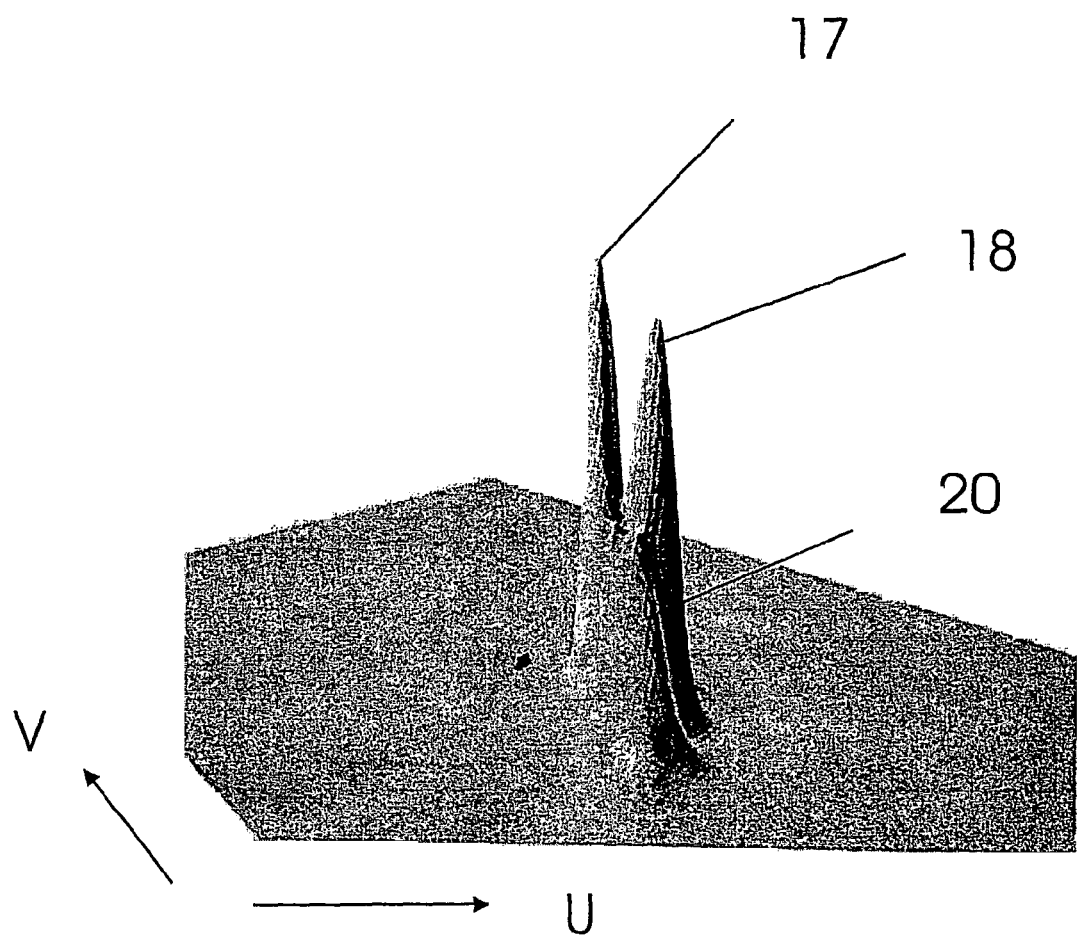
FIG. 5 depicts the two-dimensional histogram according to FIG. 3 that is overlaid with a second histogram whose of center of gravity is identical to the center of gravity of the two-dimensional histogram according to FIG. 3.

Alternatively, the frequency distributions in block 7 can also be subtracted from each other. In addition, the remaining difference can be amplified by multiplication by a predetermined factor. Small differences in color distribution 12 can be detected by this means. This is schematically depicted in FIG. 5, wherein the resulting frequency distribution 12 exhibits a diagonally sloping shoulder 20 and two peaks 17, 18.

Obviously, i moments can be calculated for the frequency distributions and compared with each other, whereby i is a whole number and i≧1. Further information about the color variances on the semiconductor substrate 21 can be obtained by this means.

The aforementioned reference regions that can be used to calculate the reference frequency distribution 12 can also be arranged in a preset geometrical configuration on the reference wafer or on the semiconductor substrate 21 to be tested. For example, inherent inhomogeneities in the thickness of the thin applied layer can occur during a processing step. For example, when spin-coating a photoresist layer, the thickness of the applied photoresist layer may be radially dependent. In such cases, it can be advantageous to use a ring-shaped area of a reference wafer or of a semiconductor substrate 21 as the reference region. The size and geometric form of the reference region may also be varied, according to the invention.

In cases of deviation of the frequency distribution 12 from the reference frequency distribution 12, a defocusing error during illumination can also be presumed. Other structures are created on the semiconductor substrate as a result of defocused illumination, which express themselves in a different frequency distribution 12.

The aforementioned method is in principle suitable for evaluating images quickly and completely automatically. As a result, the method may be combined with a method to produce structured semiconductor substrates 21, wherein the surface of the semiconductor substrate 21 is tested between two processing steps such that if the color shift or the differences in the color distribution for the semiconductor substrate 21 to be tested are determined to exceed a preset threshold, measures can be taken to ensure uniformly high quality in semiconductor production.

These measures may, for example, consist in that the semiconductor substrate that was just tested, or parts thereof that have been found to be defective, may be discarded in a subsequent processing step, or therein that the defective thin layer can be removed from the surface of the semiconductor substrate 21 by, for example, rinsing away the recently applied photoresist layer and applying a fresh thin layer thereto in the subsequent processing step, and then testing same until the applied layer is found to meet quality requirements. Such a procedure is known as "after development inspection" (ADI).

For this purpose, an alarm signal, variable, or the like can be created in case a predetermined threshold value is exceeded, which is then relayed to the CPU in the semiconductor production line, initiating the aforementioned means in the process according to the invention.

Other causes of production inhomogeneities in semiconductor components can be detected with the help of the method according to the invention. For example, the inventor determined that defocusing during stepper illumination leads to a change in the color distribution of a single SAW as a result of a differently structured surface coating on the semiconductor substrate 21. Defocusing in a single SAW during stepper illumination is comparatively costly to detect in the state of the art.

The defects that occur can be systematically distinguished as follows with the help of the method according to the invention. Said method can be used to sort individual semiconductor components or dies. Systematic global processing defects can, for example, be differentiated from localized defects. This is because if inadequately thin layers are applied over the entire surface of a wafer as a result of a systematic processing error, said systematic processing error will express itself as a color shift in all tested dies in comparison to the frequency distribution 12 of a reference wafer with known (good) surface characteristics, whereas the comparison of the frequency distributions of individual dies of one in the same wafer do not allow one to infer any significant color shift.

If a single stepper illumination area (SAW) is coated differently compared with all other areas of the same wafer, this will express itself in deviations in the corresponding SAW in comparison both from the reference histogram and from the frequency distributions of all other SAWs on the same wafer. To determine whether processing errors are limited to individual SAWs, it is therefore advantageous if the frequency distribution 12 is in each case calculated for an entire SAW for the wafer that is to be tested.

If even defects involving thin coatings on individual dies or substrates are to be detected with the help of the method according to the invention, it is advantageous if the frequency distribution 12 is in each case calculated for the die or wafer that is to be tested or for a subarea thereof.

By a suitable choice of the image area used to calculate the frequency distribution 12 of the wafer that is to be tested, as well as for the reference region used to calculate the reference histogram, the most varied requirements of semiconductor production can be flexibly implemented according to the invention.

Whereas the aforementioned image sensor detects intensities at varying wavelengths in the visible spectral region, the present invention is not limited thereto. In principle, intensities can be detected partially or completely in non-visible spectral regions as well. For example, the image sensor can determine intensities in the infrared, near-infrared, and/or ultraviolet spectral regions. Suitable imaging optics and elements that can be used in the spectral regions will be clear to a person skilled in the art examining this patent application, and they thus require no further explanation.

The method according to the invention can be realized with the help of software or a computer program with program code to implement the aforementioned processing steps, which are carried out when the software or computer program is implemented on a computer or other suitable data processor, for example on a microprocessor. The software or computer program can be stored on a storage medium such as a ROM, EPROM, EEPROM, CD-ROM, DVD, magnetic tape storage, or the like. Suitable hardware components to carry out the aforementioned computation will be clear to a person skilled in the art examining this description, and may comprise microprocessors, ASICs, or specialty signal processors.

Figure 6:
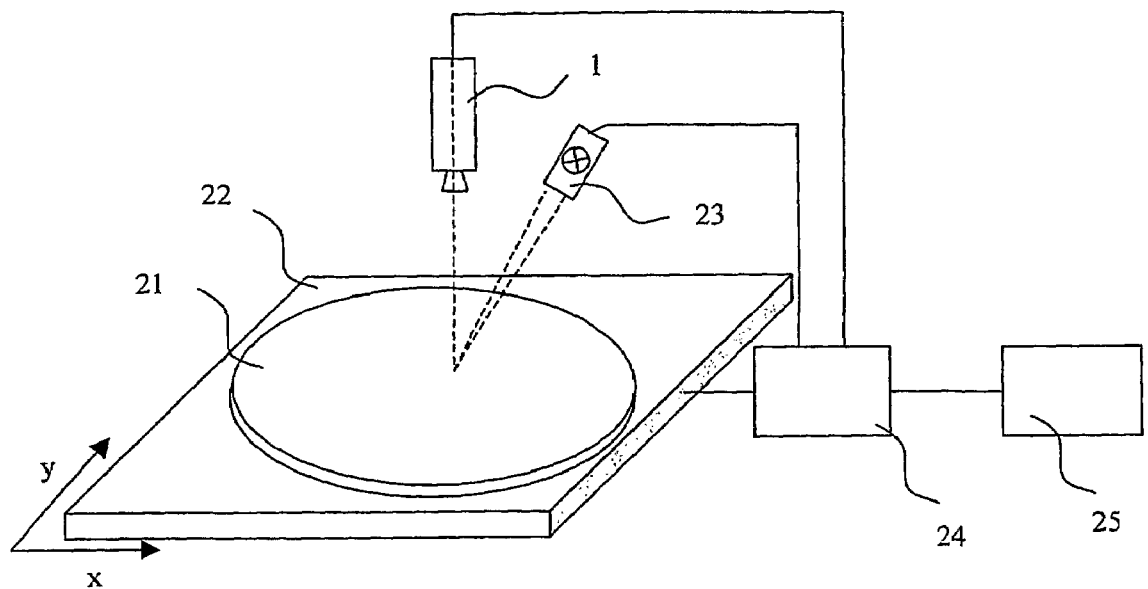
FIG. 6 depicts a schematic of an arrangement consisting of one semiconductor substrate and a camera.

FIG. 6 shows a schematic of a wafer 21 that is positioned on a scanning table 22, and whose surface is captured by a camera 1 (image sensor). Either the entire surface or only a part of the surface of the wafer 21 may be captured. In the latter case, the surface is scanned if the entire surface is to be examined. In order to generate a relative movement between the scanning table 22 and the camera 1, an x-y scanning table 22 is used that can be moved along the x and y coordinates. Said camera 1 is installed securely opposite the scanning table. Obviously, the opposite can also occur, in which the scanning table 22 is securely installed, and the camera 1 is moved over the wafer 21 for the purpose of imaging. A combination in which the camera 1 moves in one direction and the scanning table 22 moves perpendicularly thereto is also possible.

The wafer is illuminated with an illumination device 23 that illuminates at least parts of the wafer surface, e.g., an aforementioned SAW. In this case, the illumination is concentrated on the SAW. In addition, a strobe light can be pulsed to capture images on the fly, in which case the scanning table 22 or the camera 1 are moved without stopping for imaging. This enables a large wafer throughput. Obviously, the relative movement between the scanning table 22 and a camera 1 can be stopped during each imaging, and the wafer 21 can also be illuminated over its entire surface. The scanning table 22, the camera 1, and the illumination device 23 are controlled by a control unit 24. The images can be stored in a computer 25 and processed there as needed.

The invention claimed is:

1. A method for optical inspection of a surface of a semiconductor (21) in which method
  an image is captured of the surface of the semiconductor substrate (21) that comprises a plurality of pixels having at least three associated intensities of varying wavelengths that are designated as color values;
  a first frequency distribution (12) is calculated from the color values by transformation in a color range that is spanned by one intensity and by color coordinates (U, V), and whose pixels have the same color coordinate values (u, v); and
  the first frequency distribution (12) calculated in this manner is used for comparison with a second correspondingly calculated frequency distribution or a variable derived therefrom,
  wherein a center of gravity is calculated from the first calculated frequency distribution (12), and a position of the center of gravity of the first calculated frequency distribution (12) is compared with a position of a center of gravity of the second frequency distribution to detect a color shift for the semiconductor substrate (21).

2. The method according to claim 1, wherein the color values are detected in the ultraviolet, visible, and/or infrared wavelength range.

3. The method according to claim 1, wherein the color values are transformed in the color range by means of linear transformation, and the first frequency distribution (12) is calculated by adding up the frequency of the occurrence of pixels having the same color coordinate values in the color range, while neglecting the intensity of the pixels.

4. The method according to claim 1, wherein the color values of a RGB color range are transformed into a YUV color range in the presence of visible wavelengths, whereby Y corresponds to the light intensity or luminescence of the pixels, and Y is not considered in calculating the first frequency distribution (12).

5. The method according to claim 1, wherein the first frequency distribution (12) that is calculated in the color range is smoothed.

6. The method according to claim 1, wherein macroscopic images that have alternatively at least one semiconductor substrate (21) comprised of a plurality of semiconductor components or dies, or of at least one surface area (SAW) of the semiconductor substrate (21) that is illuminated in a stepper illumination step, or of a single semiconductor component or die, or of a subarea thereof, are used to calculate the first frequency distribution (12).

7. The method according to claim 1, wherein the second frequency distribution is calculated on the basis of at least one image of surface areas that exhibit a given geometric arrangement on a wafer, and are in particular radially distributed.

8. The method according to claim 1, wherein for the comparison the first calculated frequency distribution (12) is subtracted from the second frequency distribution to detect differences in the color distribution for the semiconductor substrate (21).

9. The method according to claim 8, wherein an alarm signal is generated when the detected color shift or the detected differences in color distribution exceed a preset threshold.

10. The method according to claim 1, wherein for comparison an i moment of the first calculated frequency distribution (12) is compared with an i moment of the second frequency distribution, whereby i is a whole number and $i \geq 1$.

11. The method according to claim 1, wherein the second frequency distribution is based on at least one image of a reference wafer and/or of a wafer that is to be inspected.

12. A method to produce a structured semiconductor substrate (21), by which method
  the surface of the semiconductor substrate (21) is coated with a thin layer, particularly a photoresist layer, and
  the processing steps are implemented according to claim 8 in order to detect color variances on the surface of the semiconductor substrate (21).

13. A method to produce a structured semiconductor substrate (21), by which method
  the surface of the semiconductor substrate (21) is coated with a thin layer, particularly a photoresist layer; and
  the processing steps are implemented according to claim 9 in order to detect color variances on the surface of the semiconductor substrate (21); whereby
  when the alarm signal is given, the semiconductor substrate (21) or subareas thereof are discarded in a subsequent processing step, or the
  surface of the semiconductor substrate (21) is freed of the thin layer so that it can be recoated and re-inspected before the subsequent processing step.

14. A device for the optical inspection of the surface of a semiconductor substrate (21); comprising
- an image sensor (1) to capture an image of the surface of the semiconductor substrate (21) that comprises a plurality of pixels each with at least three associated intensities of varying wavelengths that are designated as color values;
- a computational device used to calculate from the color values in a color range that spans one intensity and color coordinates (U, V) a first frequency distribution (12) of pixels having the same color coordinate values (u, v); and
- a means of comparison to use the first frequency distribution (12) that is calculated in this manner for a comparison with a second correspondingly calculated frequency distribution, or a variable derived therefrom;
- wherein the means of comparison is programmed such that it can calculate a center of gravity from the calculated first frequency distribution (12) and compare a position of the center of gravity with a position of a center of gravity of the second frequency distribution in order to detect a color shift for the semiconductor substrate (21).

15. The device according to claim 14, wherein the image sensor (1) captures the color values in the ultraviolet, visible, and/or infrared wavelength range.

16. The device according to claim 14, wherein the computational device is programmed such that the color values can be transformed by means of linear transformation in the color range, and the first frequency distribution (12) can be calculated by adding the frequency of the occurrence of pixels having the same color coordinate values in the color range, while neglecting the intensity of the pixels.

17. The device according to claim 14, wherein the computational device is programmed such that the color values of an RGB color range can be transformed into a YUV color range at visible wavelengths, whereby Y corresponds to the light intensity or luminescence of the pixels, and Y need not be considered in calculating the first frequency distribution (12).

18. The device according to claim 14, additionally comprising a filter that is used to smooth the calculated first frequency distribution (12) in the color range.

19. The device according to claim 14 in which the computational device is programmed such that calculation of the frequency distributions alternatively uses a semiconductor substrate (21) comprising at least one plurality of semiconductor components or dies; or at least one surface area (SAW) of the semiconductor substrate (21) that is illuminated in a stepper illumination step; or an individual semiconductor component or die; or a subarea thereof.

20. The device according to claim 14, wherein the computational device is programmed such that the second frequency distribution is calculated based on at least one image of surface areas that exhibit a given geometric arrangement on a wafer, and are in particular radially distributed.

21. The device according to claim 14, wherein the means of comparison is programmed such that it can subtract the first calculated frequency distribution (12) from the second frequency distribution in order to detect differences in color distribution for the semiconductor substrate (21).

22. The device according to claim 21, wherein the means of comparison is programmed such that an alarm signal is generated when the detected color shift or the detected differences in color distribution for the semiconductor substrate (21) exceed a given threshold.

23. The device according to claim 14, wherein the means of comparison is programmed such that the comparison of an i moment of the first calculated frequency distribution (12) can be compared with an i moment of the second frequency distribution, whereby i is a whole number and $i \geqq 1$.

24. A device for producing a structured semiconductor substrate (21), comprising
- a coating device to coat the surface of the semiconductor substrate (21) with a thin layer, particularly with a photoresist layer; and
- the device according to claim 21 is programmed to detect color variances on the surface of the semiconductor substrate (21).

25. A device for producing a structured semiconductor substrate (21), comprising
- a coating device to coat the surface of the semiconductor substrate (21) with a thin layer, particularly with a photoresist layer; and
- the device according to claim 22 is programmed to detect color variances on the surface of the semiconductor substrate (21); whereby the device is programmed such that when the alarm signal is given, the semiconductor substrate (21) or subareas thereof can be discarded in a subsequent processing step, or the surface of the semiconductor substrate (21) can be freed of the thin layer and recoated before the subsequent processing step.

26. A software, in particular a computer program, comprising program code to implement all steps according to claim 1 when the software or computer program is run on a computer or a data processor.

27. Software, in particular a computer program with program code according to claim 26 that can be stored on a data storage medium readable by a computer.

* * * * *